(12) United States Patent
Ishibashi et al.

(10) Patent No.: US 11,571,588 B2
(45) Date of Patent: Feb. 7, 2023

(54) CHAIR-TYPE PHOTOTHERAPY DEVICE

(71) Applicant: Teijin Pharma Limited, Tokyo (JP)

(72) Inventors: Naoya Ishibashi, Tokyo (JP); Yuki Kawase, Tokyo (JP); Takuya Nanjo, Tokyo (JP); Takamitsu Okayama, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 0 days.

(21) Appl. No.: 17/255,208

(22) PCT Filed: Jun. 27, 2019

(86) PCT No.: PCT/JP2019/025510
§ 371 (c)(1),
(2) Date: Dec. 22, 2020

(87) PCT Pub. No.: WO2020/004516
PCT Pub. Date: Jan. 2, 2020

(65) Prior Publication Data
US 2021/0268308 A1  Sep. 2, 2021

(30) Foreign Application Priority Data

Jun. 29, 2018 (JP) ............................. JP2018-124653
Sep. 28, 2018 (JP) ............................. JP2018-184666

(51) Int. Cl.
*A61N 5/06* (2006.01)
*A61G 15/00* (2006.01)
*A61B 90/00* (2016.01)

(52) U.S. Cl.
CPC ......... *A61N 5/0622* (2013.01); *A61G 15/007* (2013.01); *A61B 90/361* (2016.02);
(Continued)

(58) Field of Classification Search
CPC ... A61B 5/0077; A61B 5/4836; A61B 5/6891; A61B 5/7425; A61B 90/361;
(Continued)

(56) References Cited

U.S. PATENT DOCUMENTS

2005/0203496 A1    9/2005  Ritchie et al.
2007/0139930 A1*   6/2007  Spivak ................. A61N 5/0616
                                                362/294
(Continued)

FOREIGN PATENT DOCUMENTS

CN         2790508 Y     6/2006
CN       201974619 U     9/2011
(Continued)

OTHER PUBLICATIONS

International Search Report of PCT/JP2019/025510 dated Sep. 17, 2019 [PCT/ISA/210].
(Continued)

*Primary Examiner* — Mallika D Fairchild
*Assistant Examiner* — Shreya Anjaria
(74) *Attorney, Agent, or Firm* — Sughrue Mion, PLLC

(57) ABSTRACT

An object of the present invention is to provide a chair-type phototherapy device that enables a patient to perform light irradiation accurately targeted at a treatment site in a seated position on a chair and consequently achieves effective phototherapy even when the treatment site is in the back region that the patient is unable to see, for example, as in light irradiation for dysuria patients and patients with pain, and the patient performs light irradiation by himself/herself at home. The present invention provides a chair-type phototherapy device having a seat on which a patient is seated. The chair-type phototherapy device includes a radiation module configured to emit radiation light toward a living body, a drive module positioned behind the patient for
(Continued)

moving the radiation module, and a fixing module fixing the drive module to the seat.

14 Claims, 9 Drawing Sheets

(52) U.S. Cl.
CPC .... *A61G 2210/00* (2013.01); *A61N 2005/066* (2013.01); *A61N 2005/0626* (2013.01); *A61N 2005/0632* (2013.01); *A61N 2005/0643* (2013.01)

(58) Field of Classification Search
CPC ............ A61B 2560/029; A61G 15/007; A61G 2210/00; A61N 5/06; A61N 5/0613; A61N 5/0622; A61N 2005/0626; A61N 2005/0632; A61N 2005/0643; A61N 2005/0652; A61N 2005/066
See application file for complete search history.

(56) References Cited

U.S. PATENT DOCUMENTS

| | | | | |
|---|---|---|---|---|
| 2009/0216299 | A1* | 8/2009 | Dantus | A61N 5/0616 607/89 |
| 2013/0137992 | A1* | 5/2013 | Yamazaki | A61N 5/0619 600/476 |
| 2013/0231720 | A1 | 9/2013 | Luellau | |
| 2019/0366120 | A1* | 12/2019 | Jing | A61H 39/02 |

FOREIGN PATENT DOCUMENTS

| | | | | |
|---|---|---|---|---|
| CN | 102626540 | A | 8/2012 | |
| CN | 205108757 | U | 3/2016 | |
| CN | 205494134 | U | 8/2016 | |
| CN | 106621070 | A | 5/2017 | |
| CN | 107320133 | A | 11/2017 | |
| EP | 1262210 | A1 | 12/2002 | |
| EP | 2599469 | A1 | 6/2013 | |
| JP | 2003-019217 | A | 1/2003 | |
| JP | 2003-024458 | A | 1/2003 | |
| JP | 2009-172068 | A | 8/2009 | |
| JP | 2013-094429 | A | 5/2013 | |
| KR | 2011-0080644 | A | 7/2011 | |
| WO | 2012/014799 | A1 | 2/2012 | |
| WO | 2012/113238 | A1 | 8/2012 | |
| WO | WO-2012113238 | A1 * | 8/2012 | ........... A61N 5/0619 |
| WO | 2018/090131 | A1 | 5/2018 | |

OTHER PUBLICATIONS

Supplementary European Search Report, dated Feb. 28, 2022, issued by the European Patent Office in European Application No. 19825986.3.

Communication, dated Nov. 3, 2021, issued by The State Intellectual Property Office of People's English Republic of China in Application No. 201980044058.7; 19 pages with translation Translation.

Office Action dated Jun. 8, 2022 from the China National Intellectual Property Administration in CN Application No. 201980044058.7.

* cited by examiner

[Fig. 1]
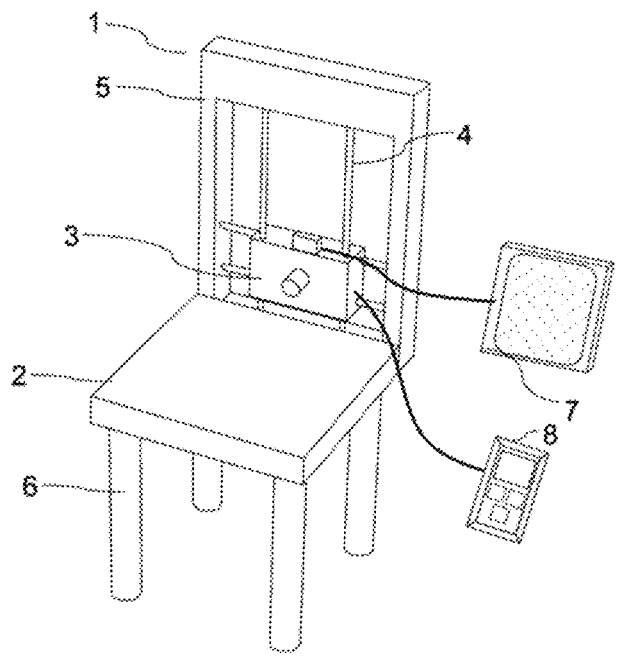
[Fig. 2]
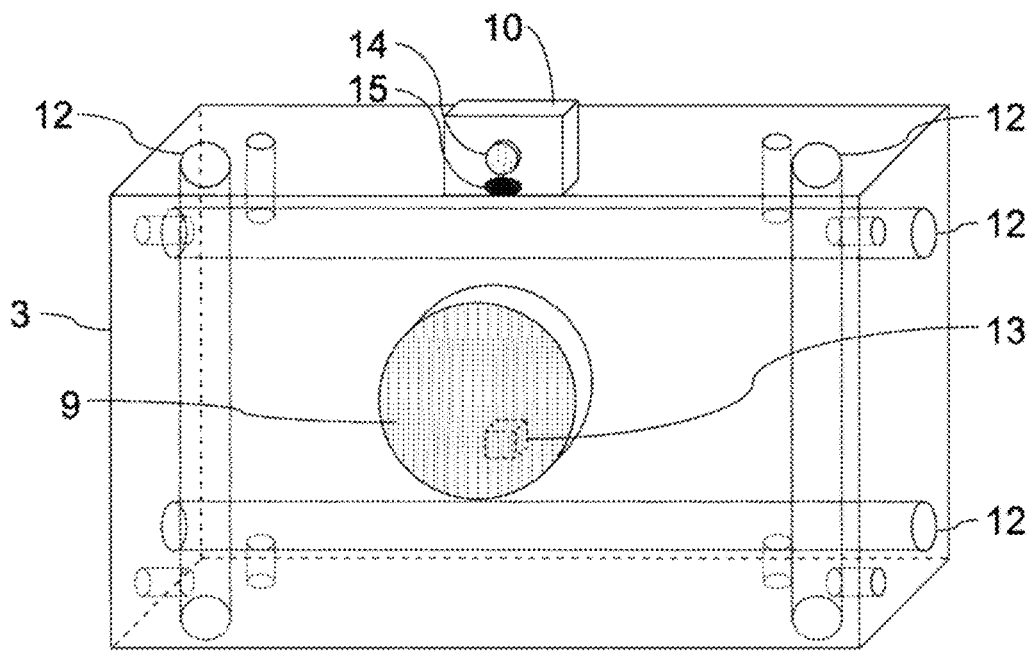

[Fig. 3]
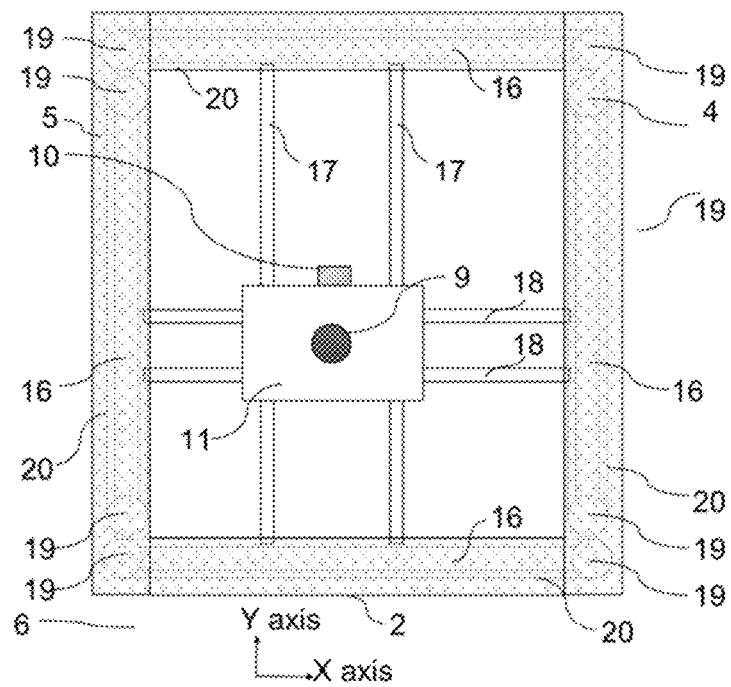
[Fig. 4]
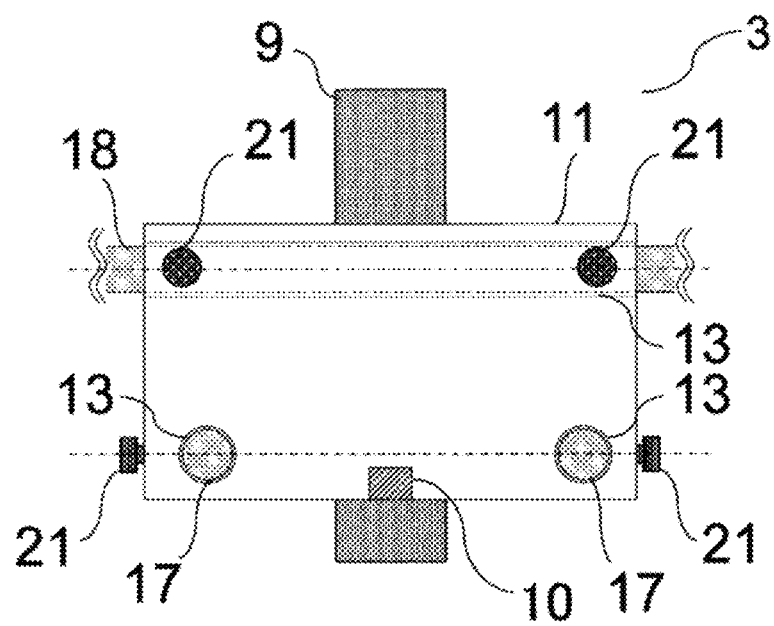

[Fig. 5]
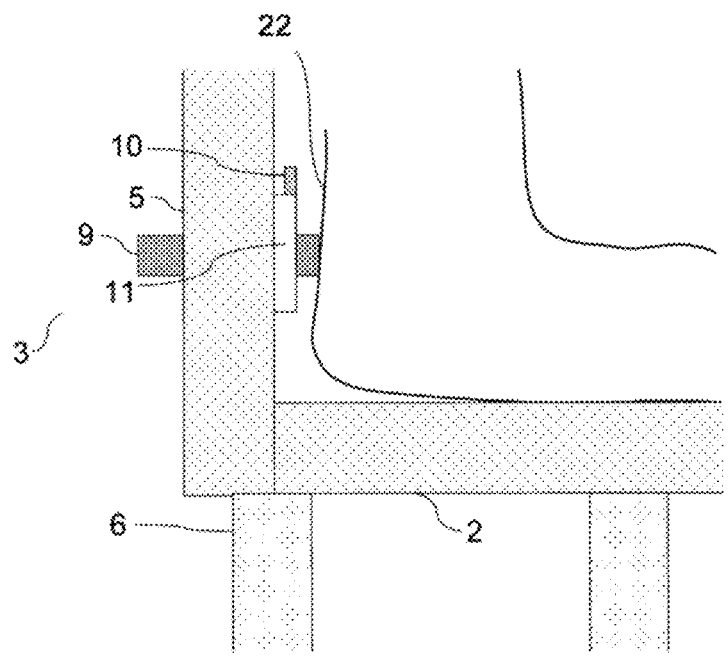
[Fig. 6]
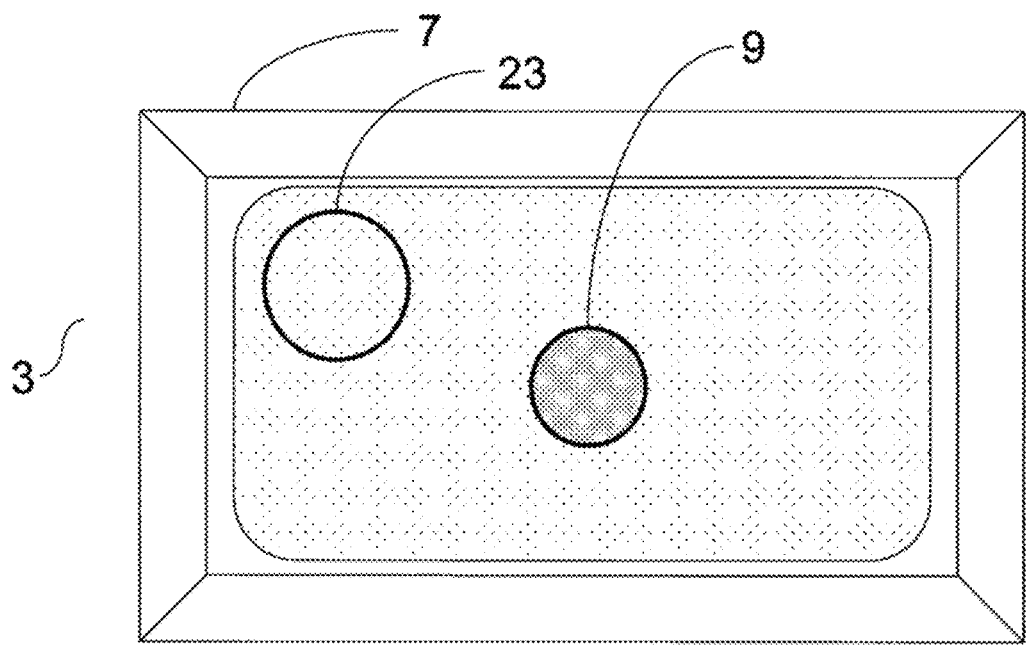

[Fig. 7]
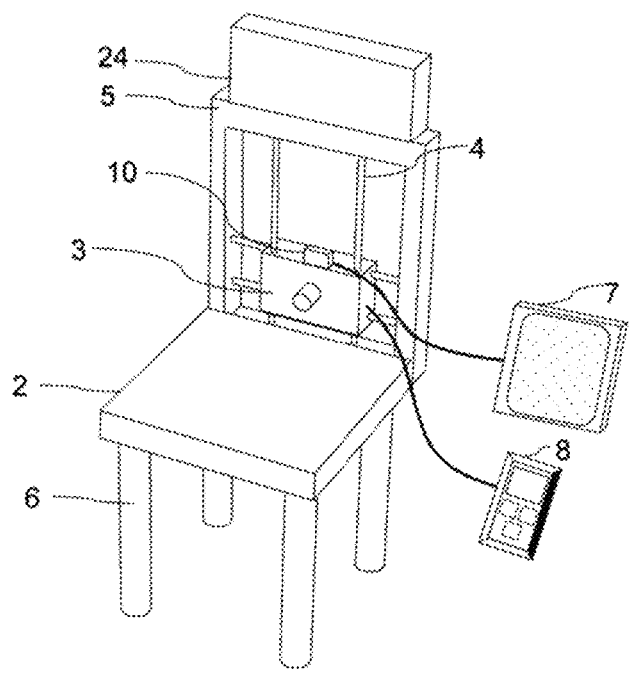
[Fig. 8]
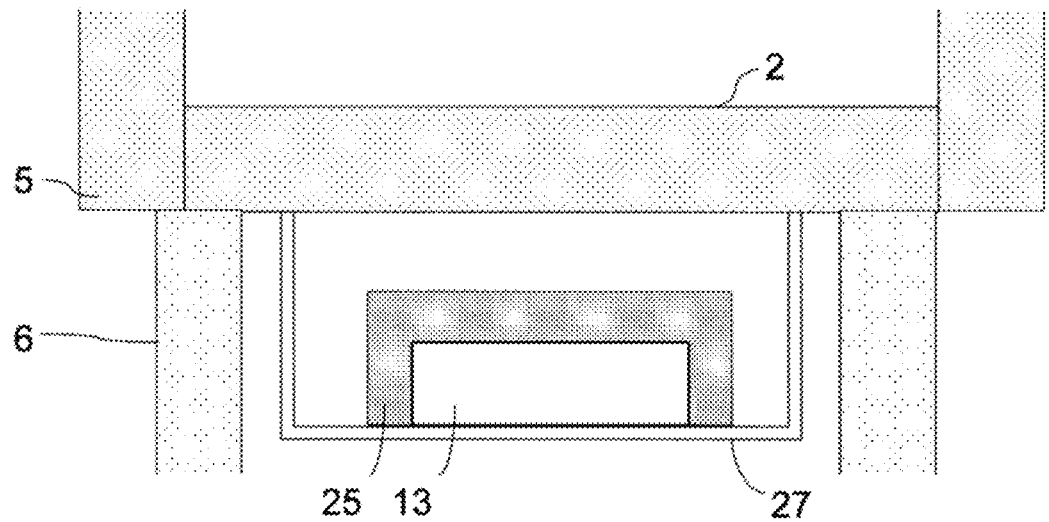

[Fig. 9]
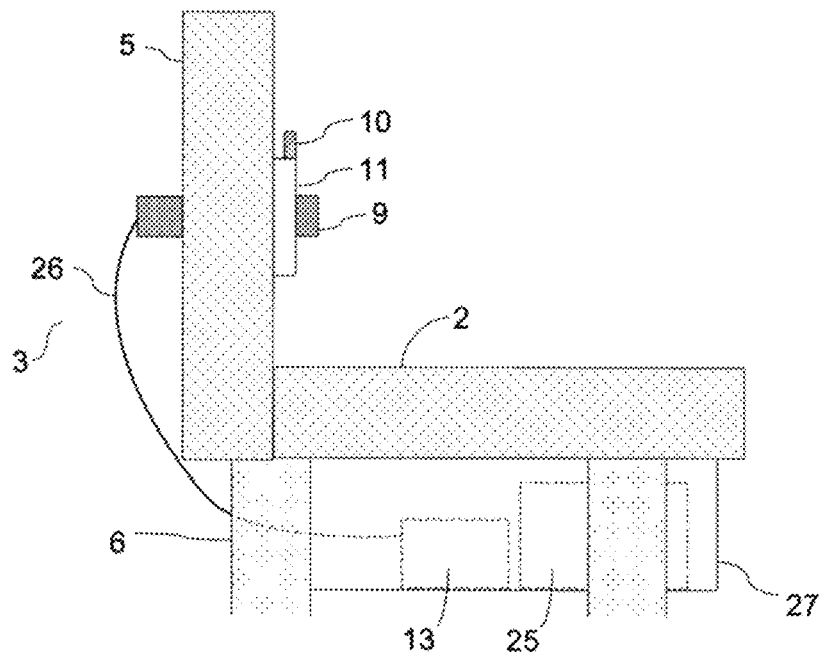
[Fig. 10]
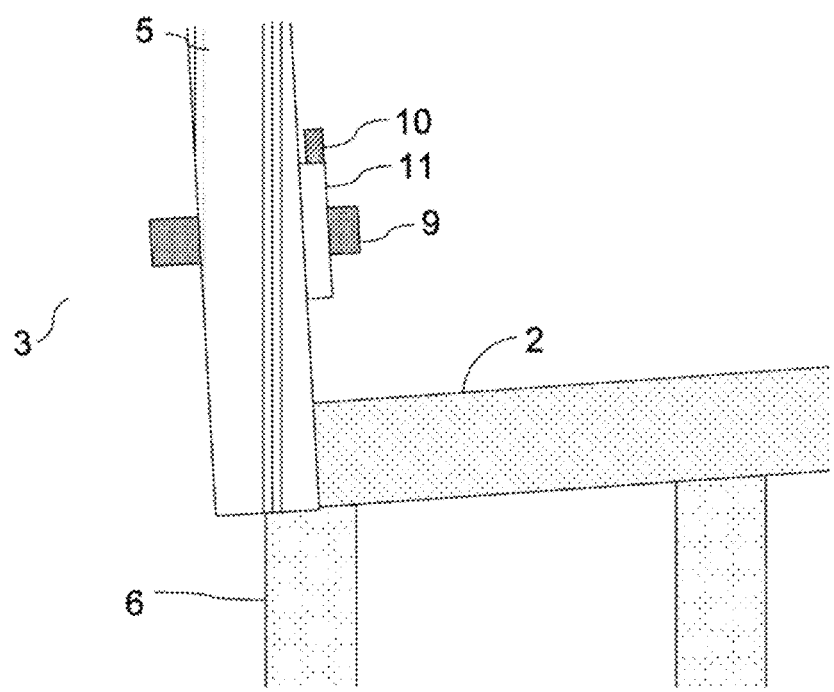

[Fig. 11]
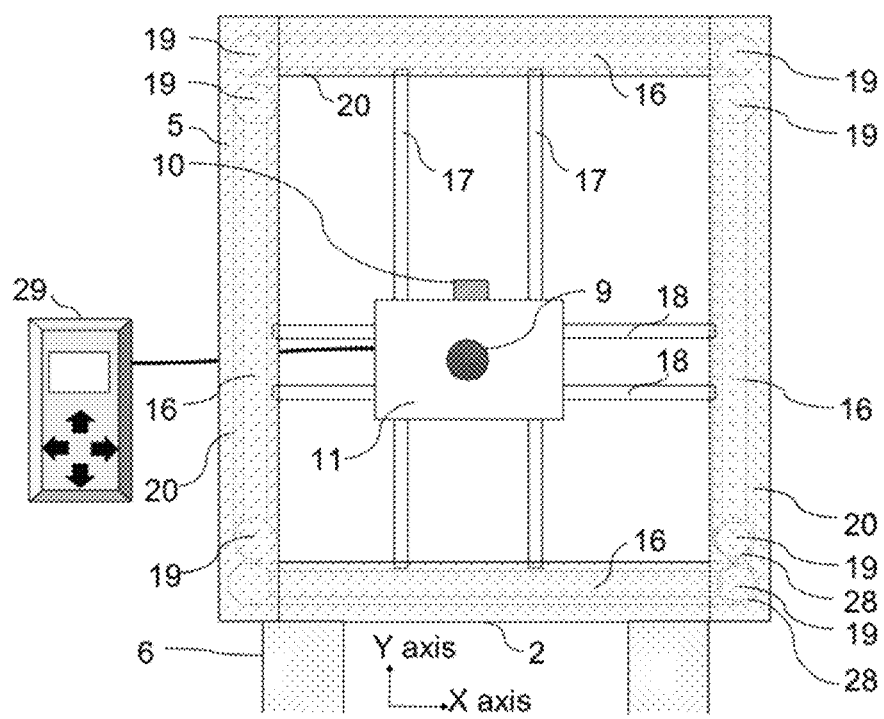

[Fig. 12]
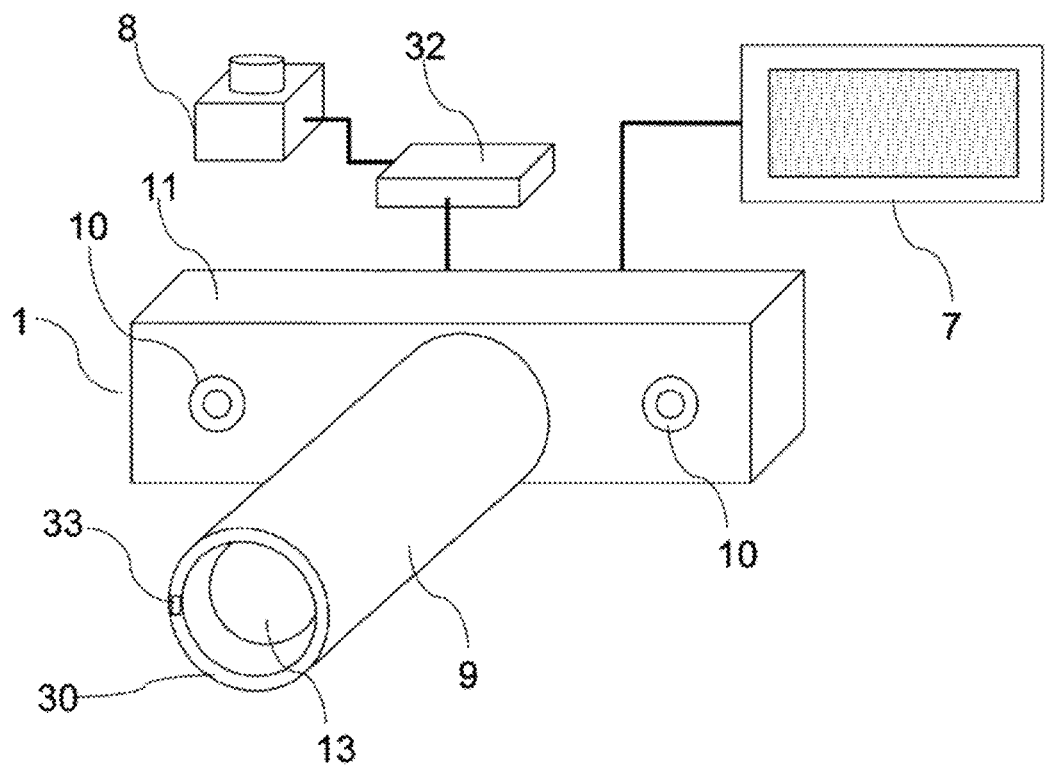
[Fig. 13]
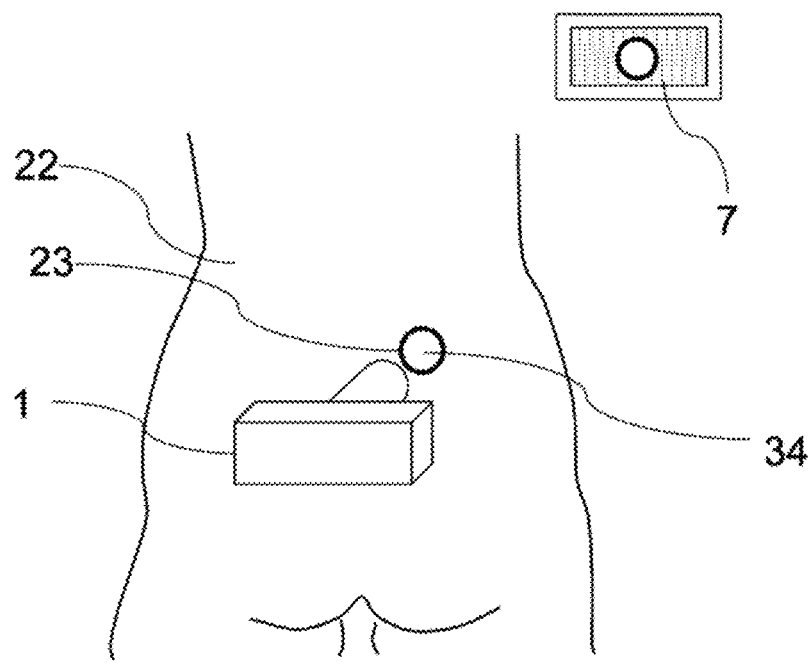

[Fig. 14]
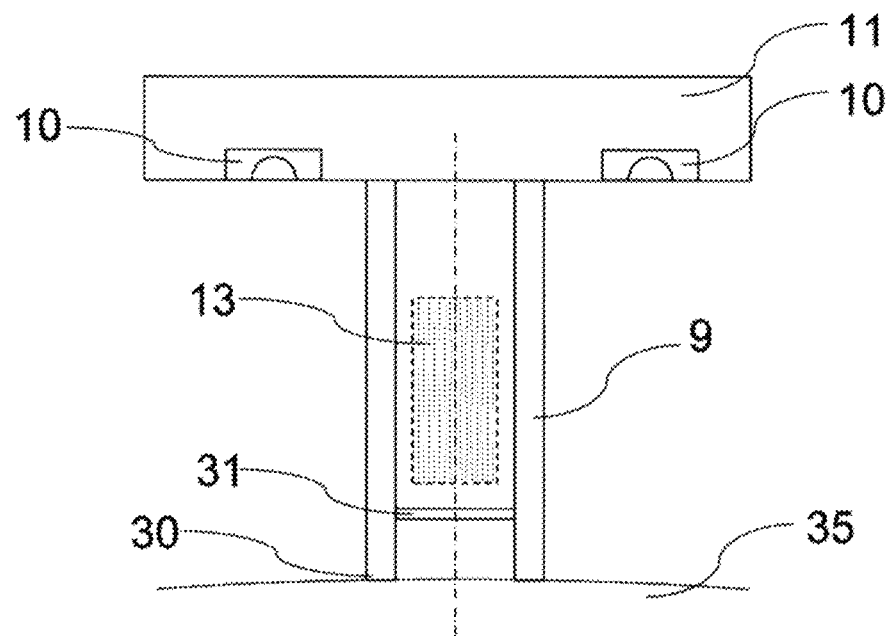
[Fig. 15]
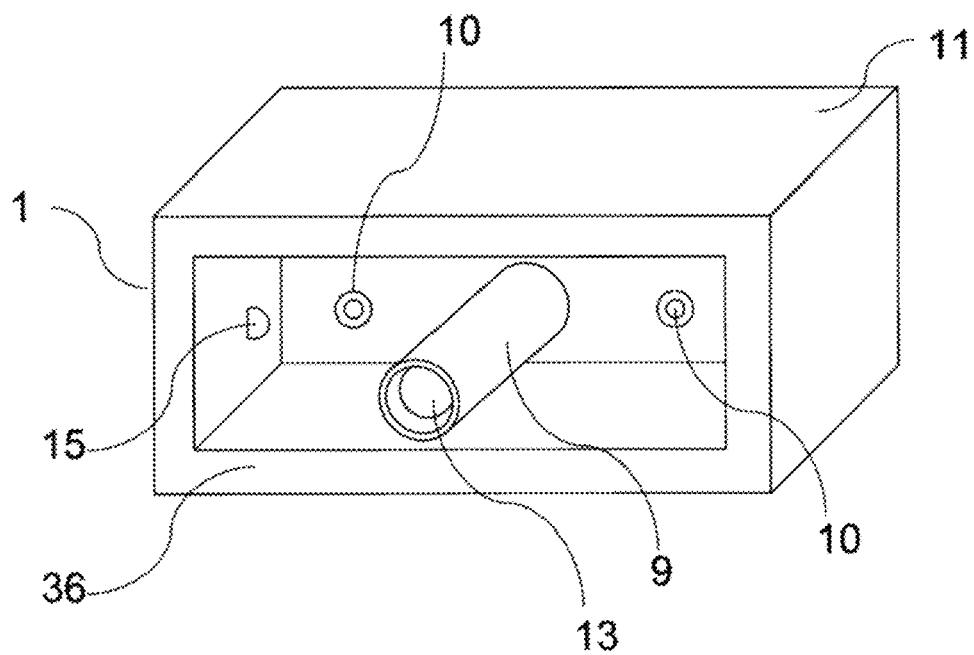

[Fig. 16]
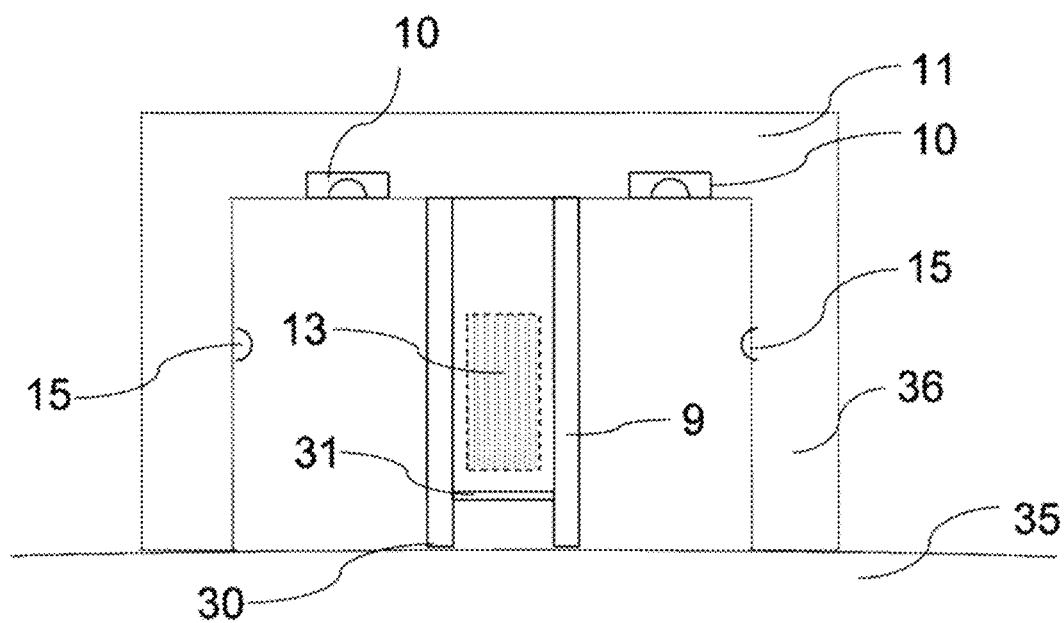

CHAIR-TYPE PHOTOTHERAPY DEVICE

CROSS REFERENCE TO RELATED APPLICATIONS

This application is a National Stage of International Application No. PCT/JP2019/025510, filed Jun. 27, 2019, claiming priorities to Japanese Patent Application No. 2018-124653, filed Jun. 29, 2018 and Japanese Patent Application No. 2018-184666, filed Sep. 28, 2018.

TECHNICAL FIELD

The present invention relates to a chair-type phototherapy device.

BACKGROUND ART

Phototherapy devices that apply, for example, infrared rays (wavelengths of approximately 700 nm to 2500 nm) as treatment light targeted at an affected area or an acupressure point through the skin have been used for treatment such as relief of aching pain. It has recently been revealed that radiation of light has various actions on nerves, such as selective suppression of nerve conduction in sensory fibers that transmit pain in peripheral nervous systems, suppression of pain-producing substances, and tension relaxation of sympathetic nerves. Among light rays, laser light is widely used in these applications since a specific wavelength can be emitted with high power. For example, PTL 1 describes treatment of dysuria, in which dysuria is treated by applying laser light through the skin, targeted at the sacral foramina where bladder sensory nerves exist, in order to suppress abnormal activities of sensory nerves in the bladder. In such treatment, repeatedly irradiating a given site such as an affected area and an acupressure point is an important factor for achieving the maximum effect. It is desirable that patients perform light irradiation by themselves at home because light irradiation for a few minutes to a few tens of minutes per day need to be repeated at a frequency of twice a week to everyday. However, it is difficult to perform light irradiation by pressing a device against a position that the patients cannot see, such as the back and the waist. Conventional photoirradiation methods for affected areas are described in PTL 2 in which a laser radiation probe is held in hand and brought into contact with an affected area and in PTL 3 in which an arm extending from a therapeutic device body is moved to a desired position and a radiation probe fixed to the tip end of the arm is used.

CITATION LIST

Patent Literature

[PTL 1] Japanese Unexamined Patent Application Publication No. 2009-172068
[PTL 2] Japanese Unexamined Patent Application Publication No. 2013-094429
[PTL 3] Japanese Unexamined Patent Application Publication No. 2003-019217

SUMMARY OF INVENTION

Technical Problem

In treatment of dysuria and pain treatment at home by light irradiation, a patient performs light irradiation by aligning an irradiation position by himself/herself on the back region such as the back and the waist to irradiate the sacral foramina with bladder sensory nerves or the spinal ganglion corresponding to a pain-causing site with light through the skin. Light irradiation to an accurate position is required to obtain sufficient therapeutic effects. For example, the patient undergoes a marking on a treatment site at hospital in advance and performs light irradiation by aligning an irradiation position of a device with the marking, thereby achieving effective phototherapy.

In the configuration of the therapeutic device in which a laser light radiation probe is held in hand and brought into contact as disclosed in PTL 2, the patient is supposed to put the arm around the back region by himself/herself and hold the radiation probe at an appropriate position in an unnatural posture for a few minutes to a few tens of minutes. In the therapeutic device having an arm as disclosed in PTL 3, the patient may perform phototherapy on the patient's back region in a seated state without putting the arm around the back, by adjusting the position of the arm and arranging the radiation probe on the back region. However, the arm may be moved and thus the irradiation position may be displaced during therapy, resulting in insufficient therapeutic effects. The patient therefore has to always maintain the same posture so as not lean on the arm, and this is far from a treatment in a comfortable position. If the treatment is unable to be performed in a comfortable posture, the burden of treatment on the patient increases to make it difficult to continue the treatment, and sufficient therapeutic effects fail to be achieved. When the device is equipped with a rotating mechanism and an expansion mechanism for freely moving the arm and a support mechanism for fixing them, the device becomes large and heavy in weight and difficult to use in a limited space such as at home.

An object of the present invention is then to provide a chair-type phototherapy device that enables a patient to perform light irradiation accurately targeted at a treatment site in a seated position on a chair and consequently achieves effective phototherapy even when the treatment site is in the back region that the patient is unable to see, for example, as in light irradiation for dysuria patients and patients with pain, and the patient performs light irradiation by himself/herself at home.

Solution to Problem

The present invention provides a chair-type phototherapy device having a seat on which a patient is seated. The chair-type phototherapy device includes a radiation module configured to emit radiation light toward a living body, a drive module positioned behind the patient for moving the radiation module, and a fixing module fixing the drive module to the seat.

Advantageous Effects of Invention

With this configuration, even when a patient has a treatment site in the back region that he/she is unable to see and performs light irradiation by himself/herself at home, by aligning the position of the radiation module with the treatment site first treated while being seated on the chair, the patient only has to be seated to position the radiation module at the treatment site with high reproducibility in the second and subsequent treatment and can perform phototherapy for a few minutes to a few tens of minutes in a comfortable posture in a seated state. As a result, appropriate treatment can be achieved.

BRIEF DESCRIPTION OF DRAWINGS

FIG. 1 is a perspective view of an embodiment of the present phototherapy device.

FIG. 2 is an enlarged view of a radiation module of the present phototherapy device.

FIG. 3 is a diagram illustrating a drive module of the present phototherapy device.

FIG. 4 is a top view of the radiation module of the present phototherapy device.

FIG. 5 illustrates a use state of the present phototherapy device.

FIG. 6 is an enlarged view of a monitor of the present phototherapy device.

FIG. 7 illustrates another embodiment of the present phototherapy device.

FIG. 8 illustrates another embodiment of the present phototherapy device.

FIG. 9 illustrates another embodiment of the present phototherapy device.

FIG. 10 illustrates another embodiment of the present phototherapy device.

FIG. 11 illustrates another embodiment of the present phototherapy device.

FIG. 12 illustrates another embodiment of the present phototherapy device.

FIG. 13 is a diagram illustrating a method of aligning position in another embodiment of the present phototherapy device.

FIG. 14 is a device cross-sectional view in another embodiment of the present phototherapy device.

FIG. 15 illustrates another embodiment of the present phototherapy device.

FIG. 16 is a device cross-sectional view in another embodiment of the present phototherapy device.

DESCRIPTION OF EMBODIMENTS

Embodiments of the present invention will be described in detail below with reference to the drawings. In a description of the drawings, the same elements are denoted by the same reference signs and an overlapping description is omitted.

Chair-Type Light Irradiation Device in the First Embodiment

A chair-type phototherapy device 1 according to a first embodiment of the present invention will be described with reference to the drawings. As illustrated in FIG. 1, the chair-type phototherapy device 1 in the present embodiment is a device for performing dysuria treatment and pain treatment by irradiating the position of the sacral foramina and the ganglion of a patient with light rays. The chair-type phototherapy device 1 includes a seat 2 on which the patient is seated, a radiation module 3, a drive module 4, and a fixing module 5.

The seat 2 has a size enough for one patient to sit on and has a substantially rectangular or substantially circular shape. The material of the seat 2 is, for example, leather or fiber for its surface, with the inside stuffed with a cushion material such as urethane and with a frame made of metal, resin, wood, or the like. A plurality of legs 6 are provided under the seat 2.

The fixing module 5 is shaped like a rectangular or square frame and holds and fixes the drive module 4 in the inside. The fixing module 5 is attached upright from the seat 2 at one end of the seat 2 of the chair and is arranged behind the back of the patient. The fixing module 5 is formed of metal, resin, wood, or the like to ensure the strength and enables the patient to perform treatment while leaning against it. The fixing module 5 is not necessarily directly fixed to the seat 2 as long as its relative position to the seat 2 is fixed. For example, the fixing module 5 may be fixed to the chair legs 6 connected to the seat 2. The fixing module 5 may be configured separately from the backrest of the chair.

In the inside of the frame shape of the fixing module 5, the radiation module 3 for irradiating the patient with light rays and the drive module 4 for changing the position of the radiation module 3 are provided. The drive module 4 can be actuated in the fixing module 5 to move the radiation module 3 to a given position. A monitor 7 is connected to the radiation module 3 to display an image in the surrounding of the treatment site.

The present chair-type phototherapy device 1 may include a remote controller 8 for irradiation control to enable light irradiation while the patient keeps a seated position. The remote controller 8 for irradiation control is connected to a casing 11 of the radiation module 3 through a not-illustrated light emission control unit via a cable and is supplied with electricity from a not-illustrated power source. In addition, the remote controller 8 for radiation control transmits a signal to the light emission control unit based on an input by the patient operating a switch on the remote controller 8 for radiation control, and the light emission control unit controls light irradiation from a radiation probe 9. For example, switching between oscillation and stop of light from the radiation probe 9 is performed. The patient thus can switch radiation in a seated position, prevent erroneous irradiation to a site other than the treatment site, and perform safe phototherapy.

FIG. 2 is a diagram illustrating the radiation module 3. The radiation module 3 includes the radiation probe 9, an observation module 10 for grasping a treatment site in the back region of the patient and an irradiation position of irradiation light, and the casing 11.

The casing 11 is a box having any shape for holding the radiation probe 9 and the observation module 10. In the horizontal direction and the vertical direction of the casing 11, any given number of through holes 12 are provided, and the through holes 12 are provided with lateral holes orthogonal to the through holes 12. The through holes 12 and the lateral holes will be described later. The casing 11 contains a not-illustrated built-in power source such as a battery for supplying electricity to the above-noted remote controller 8 for radiation control as well as the radiation module 3, the observation module 10, and the monitor 7. The power source may be provided outside of the casing 11, and the power source may include switching or other circuits. In this case, the power source is connected to the radiation module 3, the observation module 10, the monitor 7, and the remote controller 8 for radiation control by wire.

The radiation probe 9 is connected substantially to the center of the casing 11. The radiation probe 9 is a member for radiating light rays toward a given position on the patient's skin and is formed of metal, resin, or the like in the shape of a hollow cylinder. The shape of the radiation probe 9 is not necessarily cylindrical. A treatment light source 13 is provided inside the radiation probe 9. For example, a laser, an LED, a halogen lamp, and a xenon lamp can be used as the treatment light source 13. The treatment light source 13 may be installed outside the radiation probe 9 and the light may be guided to the radiation probe 9 through a light guide path such as an optical fiber.

The radiation probe 9 is fixed to the casing 11 so as to protrude from the casing 11 toward the patient. Since body shapes may vary among patients, it is preferable that the radiation probe 9 and the casing 11 are constructed such that the fixed position of the radiation probe 9 relative to the casing 11 can be adjusted, enabling to adjust the amount of protrusion of the radiation probe 9 so that the radiation probe 9 is in contact with an irradiation site without uncomfortable feeling when the patient is seated. For example, the casing 11 has a hole receiving the radiation probe 9 substantially at the center of a surface facing the patient, and the amount of protrusion of the radiation probe 9 is adjusted by fitting the radiation probe 9 in the hole and changing its attachment position. In this case, it is preferable that the casing 11 and the radiation probe 9 are connected through a ratchet mechanism such that the radiation probe 9 is movable only toward the back of the patient relative to the casing 11 and the movement in the opposite direction is restricted. This configuration can prevent dropping of the radiation probe 9 from the casing 11 even when the patient leans deeply against the radiation module 3 to push the radiation probe 9 in strongly. A rack and pinion mechanism, for example, may be used instead of the ratchet mechanism.

The observation module 10 is connected to the top portion of the casing 11. The observation module 10 includes a camera 14 and an illumination light source 15. The camera 14 is a member for grasping a treatment site and an irradiation position of radiation light in the back region of the patient. A CCD camera, a CMOS camera, and the like can be used as the camera 14. The illumination light source 15 is a member for illuminating a field of observation of the camera 14 and capturing a sharp image. An LED, a fluorescent lamp, and the like can be used as the illumination light source 15. The observation module 10 may be installed at any position in the casing 11 as long as the treatment site of the patient and the position of radiation light can be observed by the camera 14.

The image captured by the camera 14 appears on the monitor 7. The monitor 7 may be connected to the observation module 10 by wire or may be configured separately from the observation module 10 and connected to the observation module 10 through a known wireless communication technique.

FIG. 3 is a diagram illustrating the drive module 4. In the present embodiment, the drive module 4 includes four sliders 16 and at least two of linear guide 17 and linear guide 18 for two axial directions of X and Y: the X axis substantially in the horizontal direction and the Y axis direction orthogonal to the X axis. The linear guide 17 and the linear guide 18 are arranged in any two axial directions orthogonal to each other in the same plane, and the sliders 16 are disposed orthogonally to the linear guides 17 at both ends of the linear guides 17 and the linear guides 18.

The sliders 16 each include rotation axes 19 and a belt 20 and are disposed in the inside of four sides of the frame-like fixing module 5. The rotation axes 19 are fixed to the fixing module 5. The belt 20 is a strip-like member formed of metal, resin, rubber, or the like wound around at least two rotation axes 19 and is arranged to turn around the rotation axes 19. The belt 20 may be, for example, a mechanism such as a rail or a ball screw extending in one direction in one or both of the X-axis direction and the Y-axis direction. The linear guides 17 and the linear guides 18 are rod-like members formed of metal, resin, or the like fixed to the belt 20. When the belt 20 rotates in the fixing module 5, the linear guides 17 fixed to the belt 20 move in accordance with the rotation of the belt 20. The linear guides 17 thus can move in orthogonal two axial directions in the fixing module 5.

FIG. 4 is a top view of the radiation module 3 in a state in which the radiation module 3 and the linear guides 17 are connected. The linear guides 17 are inserted slidably into the through holes 12 provided in the casing 11. Bolts 21 are inserted into the lateral holes to fix or release the linear guides 17 to/from the casing 11. The bolts 21 may be fasteners such as fixing pins, wing screws, and clamps. To move the radiation module 3, first, the bolts 21 in the linear guides 17 in the X-axis direction are released, the bolts 21 in the linear guides 18 in the Y-axis direction are fixed, and the casing 11 is manually moved in the X-axis direction. The radiation module 3 thus can be moved in the X-axis direction while the position in the Y-axis direction is fixed. Subsequently, the bolts 21 in the linear guides 17 in the X-axis direction are fixed, the bolts 21 in the linear guides 18 in the Y-axis direction are released, and the radiation module 3 is moved in the Y-axis direction while the position in the X-axis direction is fixed. With this configuration, the radiation module 3 can be moved to any position in the fixing module 5.

The configuration of the drive module 4 is not limited to the embodiment described above. For example, the following mechanism may be adopted, wherein an arm rotatable in a desired direction is attached in the vicinity of a joint section of the fixing module 5 and the seat 2, and the radiation probe 9 is attached to a tip of the arm to position the radiation probe 9 in any position in the fixing module 5. Alternatively, the following configuration may be adopted, wherein a motor is built in the rotation axis 19 to enable rotary drive, the rotation axis 19 is engaged with the belt 20, and the motor is actuated to move the belt 20. Further, the following configuration may be adopted, wherein, instead of the motor, gas cylinders or hydraulic cylinders are built in the fixing module 5 in X and Y two directions, and the translational motion of the cylinder is converted into rotational motion using gears or the like and transmitted to the rotation axes 19 to rotate.

Method for Using Chair-Type Light Irradiation Device According to an Embodiment

Referring to FIG. 5, a specific method for using the present therapy device will be described. First, the patient is seated on the seat 2 and leans against the fixing module 5. The patient moves the radiation module 3 as described above such that the radiation module 3 faces a marking 23 put on the back of the patient in advance in the patient back region 22 and makes fine adjustment of the position of the radiation module 3 while viewing the monitor 7 on which an image captured by the observation module 10 appears. Alternatively, the position of the body may be finely adjusted to align the position of the marking 23 with the radiation module 3. As illustrated in FIG. 6, the camera 14 is arranged such that the radiation probe 9 of the radiation module 3 always appears at the center of the monitor 7 to align the position of the marking 23 with the radiation probe 9 on the monitor 7. Subsequently, the loosened bolts 21 are tightened and the radiation module 3 is fixed to the drive module 4 to complete the position alignment. After the position alignment is performed, the remote controller 8 for radiation control is operated to start treatment (start light irradiation). For the treatment, preferably, light irradiation for a few minutes to a few tens of minutes per day is repeated at a frequency of twice a week to every day.

Hardware Configuration of the Second Embodiment

FIG. 7 is a diagram illustrating another embodiment of the present chair-type phototherapy device 1. Since there are many parts overlapping with other embodiments, only the parts characteristic to the present embodiment are described below and other description on the configuration is omitted. In the present embodiment, a backrest 24 of the chair is coupled to the upper side of the fixing module 5 or between the fixing module 5 and the seat 2. The material of the backrest 24 is, for example, leather or fiber for its surface, with the inside stuffed with a cushion material such as urethane and with a frame made of metal, resin, wood, or the like. The patient can lean against the backrest 24 to keep a more comfortable posture during treatment and undergo treatment for a longer time.

Hardware Configuration of the Third Embodiment

FIGS. 8 and 9 are diagrams illustrating another embodiment of the present chair-type phototherapy device 1. When the treatment light source 13 or a power source 25 is provided in the casing 11, the radiation module 3 is larger and heavier in weight, and the chair-type phototherapy device 1 as a whole has a larger size. In the present embodiment, therefore, the treatment light source 13 and the power source 25 are present independently of the radiation module 3, and the treatment light source 13 is connected to the radiation probe 9 using a probe cable 26 incorporating an optical fiber or the like for guiding light. The chair-type phototherapy device 1 according to the present embodiment has a storage unit 27 under the seat 2, and in the storage unit 27, the treatment light source 13 and the power source 25 are located. The storage unit 27 is arranged so as to be suspended below the seat 2. The storage unit 27 has a substantially cuboid shape, and by opening any one of the side surfaces thereof, the power source 25, accessories, and the like can be installed inside. Since the treatment light source 13 and the power source 25 are separate from the radiation module 3, the chair-type phototherapy device 1 as a whole can be reduced in size, and the chair-type phototherapy device 1 can be installed even in a narrow space at home, for example. When the treatment light source 13 alone is lightweight and compact, the treatment light source 13 may be installed in the radiation module 3, and only the power source 25 may be separate from the radiation module 3 and installed in the storage unit 27.

Since the chair-type phototherapy device 1 is equipped with articles such as the radiation module 3 and the drive module 4 on the back of the chair, the center of gravity is shifted to the back side, leading to lack of stability and concern about overturn of the chair. Then, heavy articles such as the treatment light source 13 and the power source 25 are installed in the storage unit 27 under the seat 2, so that the center of gravity is shifted to a lower position at the center, thereby creating stability and preventing overturn. When the power source 25 is installed in the storage unit 27, the power source 25 is covered with a cuboid box made of resin or the like to contain electronic parts, circuit boards, and the like in the inside. The power source 25 is connected to the radiation probe 9, an actuator 28, and the remote controller 8 for radiation control, a remote controller 29 for drive control, or a remote controller for operation of an integrated controller thereof, described later, through a cable and performs power supply. The device is controlled based on a signal transmitted from each remote controller, which will be detailed later.

Hardware Configuration of the Fourth Embodiment

FIG. 10 is a diagram illustrating another embodiment of the present chair-type phototherapy device 1. In the present embodiment, when the direction in which the radiation module 3 and the fixing module 5 are installed is set as the rear side and the opposite direction thereto is set as the front side for the chair-type phototherapy device 1, the seat 2 is inclined downward from the front side to the rear side. The downward inclination of the seat 2 enables the patient to sit back on the chair comfortably and makes the sitting more comfortable, and in addition, the seated position is set at a deep position on the rear side of the seat 2 in each time of treatment, thereby improving the reproducibility of positioning of the radiation probe 9 at the treatment site. The preparation work for positioning before treatment thus can be simplified. The downward inclination of the seat 2, for example, between 5° and 20° makes the sitting comfortable and sets the seated position at a deep position on the rear side of the seat 2.

Hardware Configuration of the Fifth Embodiment

FIG. 11 is a diagram illustrating another embodiment of the present chair-type therapy device. In the present embodiment, the drive module 4 includes the actuator 28 for moving the slider 16 and the remote controller 29 for drive control for controlling the actuator 25 illustrated in FIG. 11. The actuator 28 is contained in the inside of the seat 2 and may be, for example, a motor, and the rotation of the motor drives the rotation axis 19 rotatably arranged in the fixing module 5, whereby the radiation module 3 can be moved to any position in the fixing module 5 through the linear guides 17. For example, when the radiation module 3 is moved in the X direction, the sliders 16 in the X direction are driven through the actuator 25, the casing 11 slides on the linear guides 17 in the X-axis direction, and the linear guides 18 in the Y-axis direction move together with the casing 11, thereby moving the radiation module 3.

The remote controller 29 for drive control is connected to the power source 25 through a cable and is supplied with electricity, and transmits a signal to the actuator 28 based on an input which the patient makes by operating a switch on the remote controller 26 for drive control and thus controls the operation of the actuator 28. The operation is transmitted to the drive module 4 through the sliders 16 built in the seat 2. For example, target coordinates to which a stage is moved are input, and the stage is moved to the designated position. This allows the patient to adjust an irradiation position each time in a seated state, achieves more accurate positioning, and suppresses reduction in therapeutic effects due to displacement of the irradiation position.

The remote controller 8 for radiation control and the remote controller 29 for drive control may be a single remote controller for operation that contains the both functions. Operating two remote controllers is cumbersome, and one remote controller serving for radiation control and drive control facilitates operation for the patient.

Hardware Configuration of the Sixth Embodiment and Method for Using the Same

The sixth embodiment of the present invention will be described with reference to FIG. 12. In the present embodiment, the chair-type phototherapy device 1 is a device for performing treatment of dysuria by irradiating the position of the sacral foramina of the patient with light rays. The chair-type phototherapy device 1 includes a casing 11, a radiation probe 9, a treatment light source 13, and an observation module 10.

The casing 11 is formed of metal, resin, or the like in the shape of a substantially cuboid. A not-illustrated power source 25 is provided in the inside of the casing 11, and electricity is supplied from the power source 25 to the treatment light source 13, a camera 14 in the observation module 10, and a monitor 7. The power source 25 may be a battery or may be connected to an external power source by wire.

The radiation probe 9 is connected substantially at the center of a surface of the casing 11. The radiation probe 9 is formed of metal, resin, or the like in the shape of a hollow cylinder. However, the shape is not necessarily cylindrical.

Although not illustrated in FIG. 12, also in the present embodiment, the casing 11 has any given number of through holes 12 in the horizontal direction and the vertical direction, and the through holes are provided with lateral holes orthogonal to the through holes 12.

The treatment light source 13 is arranged in the radiation probe 9 such that its front end is arranged in the inside of the hollow cylindrical radiation probe 9 and behind the plane that is flush with the front end, of the side not connected to the casing 11, of the radiation probe 9.

A variety of lamps such as a laser, an LED, and a halogen lamp can be used for the treatment light source 13. The treatment light source 13 is arranged such that radiation light passes along the center axis of the cylindrical radiation probe 9 and irradiates a treatment site of the body.

A transmission window 31 is provided at the front end of the treatment light source 13 to allow radiation light emitted from the treatment light source 13 to pass through. The transmission window 31 may be made of a light-transmitting material, such as glass and plastic films, that allows radiation light to pass through.

The remote controller 8 for radiation control is connected to the casing 11 through a light emission control unit 32 via a cable. The patient operates a switch on the remote controller 8 for radiation control to transmit a signal to the light emission control unit 32 to give an instruction for oscillation and stop of light irradiation of the treatment light source 13. The remote controller 8 for radiation control may be connected to the light emission control unit 32 through well-known wireless communication.

A sensor 33 is mounted on a radiation probe front end portion 30. The sensor 33 is a sensor 33, for example, for detecting that an object comes into contact. When the radiation probe front end portion 30 comes into contact with the patient's body, the sensor 33 detects it and transmits a signal to the light emission control unit 32.

The light emission control unit 32 controls light irradiation of the treatment light source 13. Light irradiation is oscillated only when both of a signal to give an instruction to oscillate light irradiation from the remote controller 8 for radiation control and a signal indicating detection of contact from the sensor 33 are received. When a signal is not obtained from either one of them, light irradiation is stopped.

With this configuration, light is not emitted in a state in which the radiation probe front end portion 30 is detached from the body, and radiation is enabled only in a contact state, so that erroneous exposure of eyes to light irradiation, for example, can be prevented, and thus safe phototherapy can be achieved.

In the configuration of the radiation probe 9 and the treatment light source 13 described above, radiation light is emitted only in a state in which the radiation probe front end portion 30 is in contact with the patient's body. Since the treatment light source 13 is arranged behind the radiation probe front end portion 30, a radiation field 34 (a range irradiated with radiation light) on the body irradiated with radiation light is always covered with the radiation probe 9 when emission from the treatment light source 13 is permitted by the sensor 33. Therefore, leakage of radiation light from the treatment light source 13 and reflected light from the radiation field 34 to the outside of the radiation probe 9 can be prevented.

The observation module 10 is an imaging device that observes a contact region of the body with the radiation probe 9 (radiation probe front end portion 30). The patient performs position alignment of the chair-type phototherapy device 1 to an appropriate position for emitting radiation light while viewing on the monitor 7 an image captured by the observation module 10.

The observation module 10 is provided behind the radiation probe front end portion 30 and on the outside of the radiation probe 9. In FIG. 12, the observation module 10 is provided on the outside of the radiation probe 9 in the same plane as the surface of the casing 11 to which the radiation probe 9 is connected. The observation module 10 is attached so as to capture an image in the surrounding of the radiation probe front end portion 30. The observation module 10 may be provided on a plane different from the surface of the casing 11 to which the radiation probe 9 is connected or may be arranged so as to protrude from any surface on the casing 11. In the present embodiment, the observation module 10 has the camera 14, and a CCD camera 14, a CMOS camera 14, and the like can be used. Although two cameras are installed in FIG. 12, the number is not limited and one or three or more cameras may be installed. However, it is preferable that a plurality of cameras 14 are provided rather than one, because if so, an image of the entire outer periphery of the radiation probe 9 can be captured by the cameras 14 and thus the position alignment of the body with the radiation probe 9 can be performed more accurately.

Since the observation module 10 is provided behind the radiation probe front end portion 30 and on the outside of the radiation probe 9, the observation module 10 does not come into contact with the patient's body when the radiation probe front end portion 30 is not in contact with the body. In addition, since this configuration prevents the radiation light emitted from the treatment light source 13 and the reflected light thereof from leaking out of the radiation probe 9 as described above, the reflected light from the radiation field 34 is not incident on the observation module 10 installed on the outside of the radiation probe 9. This configuration therefore prevents halation otherwise caused by the observation module 10 due to the reflected light from the radiation field 34.

The monitor 7 is a display device for displaying an image captured by the observation module 10. The monitor 7 may be connected to the observation module 10 through the casing 11 by wire or may be configured separately from the casing 11 and connected to the observation module 10 through a known wireless communication technique.

A method for using the chair-type phototherapy device 1 according to the embodiment will be described with reference to FIG. 13. FIG. 13 illustrates a state in which the patient at home adjusts the position of the chair-type phototherapy device 1 in alignment with the marking 23 given at hospital or clinic and performs light irradiation.

First, a treatment site of the patient to be subjected to light irradiation is specified under a doctor's diagnosis at hospital or clinic. For example, in the treatment of dysuria by photoirradiation, the sacral foramina where bladder sensory nerves exist is targeted and irradiated with light through the skin in order to suppress abnormal activities of sensory nerves in the bladder. Since appropriate treatment requires accurately targeting the sacral foramina the position of the sacral foramina to be irradiated with light in the patient back region 22 is specified, for example, by palpation or X-ray fluoroscopy.

Subsequently, a doctor or other health professional puts a marking 23 on the specified treatment site. Ink or an adhesive sheet can be used as a material of the marking 23. In the treatment of, for example, dysuria by photoirradiation, it is preferable to repeat light irradiation for a few minutes to a few tens of minutes per day at a frequency of twice a week to every day, and it is desirable that the patient performs light irradiation by himself/herself at home. For this, the doctor specifies the sacral foramina at hospital and puts a marking 23 on the skin 35 immediately above to indicate the irradiation position and the irradiation range, and the patient refers to the marking 23 to appropriately arrange the radiation probe 9 (radiation probe front end portion 30) of the chair-type phototherapy device 1 at home to perform light irradiation.

Subsequently, for example, at home, the patient performs light irradiation by himself/herself using the chair-type phototherapy device 1. In doing so, the patient fixes the radiation module 3 of the chair-type phototherapy device 1 in alignment with the marking 23 given at hospital or clinic. When the treatment site is at the patient back region 22 and the patient is unable to see it by himself/herself, the patient views an image captured by the observation module 10 on the monitor 7 to adjust the position of the radiation module 3 such that the marking 23 and the radiation probe 9 are fitted in a given position. For example, the position between the radiation module 3 and the body is adjusted such that the cylinder of the radiation probe 9 is fitted in the hollow circular shape of the marking 23. If the marking 23 is hidden under the radiation probe front end portion 30 when the radiation probe front end portion 30 comes into contact with the patient's skin 35, accurate position alignment is difficult, and, therefore, it is desirable that the marking 23 has such a shape that avoids the radiation probe front end portion 30. An example is a hollow circular shape having a radius larger than the radius of the radiation probe front end portion 30, although the embodiment is not limited thereto.

Here, when the affected area is irradiated with light from the treatment light source 13, part of the irradiated light is reflected by the skin 35 and diffuses into the surrounding. If this reflected light is incident on the observation module 10, the observation module 10 causes halation to obscure the captured image.

Then, the present embodiment is configured such that the radiation probe front end portion 30 comes into contact with the patient's skin 35 so that the radiation field 34 is covered with the radiation probe 9. FIG. 14 is a cross-sectional view as viewed from above (the patient's head side) in FIG. 13, illustrating the radiation module 3 pressed against the skin 35. In the present embodiment, when the radiation probe front end portion 30 is not in contact with the skin 35, light is not emitted from the treatment light source 13 as described above. Therefore, in the configuration in FIG. 14, when light is emitted from the treatment light source 13, the radiation probe front end portion 30 is pressed against the skin 35 to close a gap between the radiation probe front end portion 30 and the skin 35, thereby preventing leakage of reflected light out of the radiation probe 9. Halation by the observation module 10 due to reflected light therefore can be prevented.

Further, when the radiation probe 9 is aligned with the marking 23 and the radiation probe front end portion 30 is in contact with the skin 35, the radiation field 34 does not appear in the image captured by the observation module 10 but the outer edge of the radiation probe 9 and the marking 23 appear. While viewing this image, the patient adjusts the position of the chair-type phototherapy device 1 such that the edge of the radiation probe 9 is matched with the marking 23. With this configuration, even when the treatment site is the patient back region 22 that the patient is unable to see and the patient performs light irradiation by himself/herself, for example, at home the patient can perform position alignment and fixing of the device to the treatment site accurately and easily. As a result, light irradiation accurately targeted at the sacral foramina can be performed, and appropriate treatment can be achieved. The chair-type phototherapy device 1 therefore can be widely used for, for example, dysuria patients.

Hardware Configuration of the Seventh Embodiment

The chair-type phototherapy device 1 according to a seventh embodiment of the present invention will be described with reference to FIG. 15.

In the configuration in which external light is directly incident on the observation module 10 as in FIG. 14, the observation module 10 is directly influenced by variation in the quantity of external light, which may obscure an image. For example, when the surrounding illumination blinks on and off, an image of the observation module 10 flickers and is hard to see, making the position alignment operation difficult.

In the radiation module 3 and the observation module 10 of the chair-type phototherapy device 1 according to the seventh embodiment, a casing protrusion portion 36 having a shape surrounding the radiation probe 9 is provided on the outer peripheral side of the radiation probe 9 on a connection surface on which the treatment light source 13 and the radiation probe 9 are connected to the casing 11. Further, the front end of the casing protrusion portion 36 is positioned in flush with the radiation probe front end portion 30 or positioned slightly behind the radiation probe front end portion 30. Although the casing protrusion portion 36 is a cuboid in FIG. 15, it may have, for example, a cylindrical shape.

An observation illumination light source 15 for illuminating the skin 35 is provided in the inside of the casing protrusion portion 36. The illumination light source 15 is supplied with electricity from the not-illustrated power source 25 provided in the inside of the casing 11 and is turned on and off by a switch for the power source 25. The installation position of the illumination light source 15 is not limited to on the inner side of the casing protrusion portion 36, and the illumination light source 15 may be arranged on the connection surface of the casing 11 to which the observation module 10 and the radiation probe 9 are connected. Although the case of two illumination light sources 15 arranged is illustrated in FIG. 15, one or two or more illumination light sources 15 may be installed.

FIG. 16 is a cross-sectional view as viewed from above, illustrating the casing protrusion portion 36 and the radiation probe front end portion 30 pressed against the skin 35 in a positional relation in which the front end of the casing protrusion portion 36 is flush with the radiation probe front end portion 30. This configuration eliminates a gap between the skin 35 and the casing protrusion portion 36 under the condition of the radiation probe front end portion 30 being in contact with the skin 35, and therefore can prevent intrusion of external light into the observation module 10. However, when external light does not enter the inside of the casing protrusion portion 36, an image of the inside of the casing protrusion portion 36 is unable to be obtained with the observation module 10. The marking 23 on the skin 35 and the radiation probe 9 therefore are illuminated by the illumination light source 15 provided in the inside of the casing protrusion portion 36. A clear image thus can be captured by the observation module 10 to enable the patient to perform position alignment operation of the chair-type phototherapy device 1 more easily and accurately, independently of surrounding brightness. As a result, light irradiation accurately targeted at the sacral foramina can be performed, and appropriate treatment can be achieved.

In the case where the casing protrusion portion 36 is positioned slightly behind the radiation probe front end portion 30, a minute gap is produced between the casing protrusion portion 36 and the skin 35 when the radiation probe front end portion 30 is in contact with the skin 35. However, since the casing protrusion portion 36 prevents external light from being directly incident on the observation module 10, a clear image not affected by external light can be captured as above.

In the embodiments of the present invention described above, the chair-type phototherapy device 1 has been described as a device for performing treatment of dysuria by irradiating the position of the sacral foramina of the patient with light rays. However, the present invention is not limited thereto and is applicable similarly to any phototherapy device as long as the light irradiation site is at a position that the patient is unable to see and the patient need to perform position alignment by himself/herself. The present invention is not limited to the foregoing embodiments and is susceptible to various modifications.

REFERENCE SIGNS LIST 1 chair-type phototherapy device
2 seat
3 radiation module
4 drive module
5 fixing module
6 leg
7 monitor
8 remote controller for radiation control
9 radiation probe
10 observation module
11 casing
12 through hole
13 treatment light source
14 camera
15 illumination light source
16 slider
17 linear guide
18 linear guide
19 rotation axis
20 belt
21 bolt
22 patient back region
23 marking
24 backrest
25 power source
26 probe cable
27 storage unit
28 actuator
29 remote controller for drive control
30 barrel front end portion
31 transmission window
32 light emission control unit
33 sensor
34 radiation field
35 skin
36 casing protrusion portion

The invention claimed is:

1. A chair-type phototherapy device having a seat on which a patient is to be seated, the chair-type phototherapy device comprising:
   a radiation module configured to emit radiation light toward a body of the patient, and comprising:
      a casing,
      a radiation probe which is formed as a protrusion, is disposed in the casing, and comprising a radiation probe front end portion configured to contact the patient, and
      a camera disposed at the casing and configured to acquire at least one image of a treatment site in a back region of the patient and a radiation position of the emitted radiation light;
   a monitor configured to display the at least one image acquired by the camera, to enable observation of the treatment site and the radiation position;
   a driver positioned behind the radiation module and configured to move the radiation module;
   a frame configured to fix the driver to the seat; and
   a ratchet mechanism which connects the radiation probe to the casing and configured to move the radiation probe with respect to the casing in a front direction extending away from the driver and in a rear direction opposite to the front direction,
   wherein, by moving the radiation probe in the front direction, the radiation probe front end portion is configured to be brought in contact with the patient, and
   wherein a movement of the radiation probe in the rear direction is limited such that the radiation probe is prevented from falling out from the casing.

2. The chair-type phototherapy device according to claim 1, wherein the driver includes:
   a slider fixed to the frame, and
   a linear guide connected to the slider, and
   wherein the radiation module is connected to the linear guide.

3. The chair-type phototherapy device according to claim 2, wherein the linear guide is one of at least two linear guides, and
   wherein the at least two linear guides are arranged in any two axial directions orthogonal to each other in a same plane.

4. The chair-type phototherapy device according to claim 1, further comprising:
   a treatment light source and a power source that are provided separately from the radiation module; and
   a storage unit provided under the seat,
   wherein at least one from among the treatment light source and the power source is stored in the storage unit.

5. The chair-type phototherapy device according to claim 1, wherein the frame is attached to a back end side of the seat, and the seat is inclined downward from a front side toward a rear side.

6. The chair-type phototherapy device according to claim 1, wherein the driver further includes an actuator for moving the radiation module, and wherein a remote controller is provided for controlling the actuator.

7. The chair-type phototherapy device according to claim 1, further comprising a backrest coupled to the frame.

8. The chair-type phototherapy device according to claim 1, wherein the radiation probe front end portion is configured to be aligned with a marking on the body, wherein the camera is positioned behind the radiation probe front end portion on an outside of the radiation probe, the radiation probe front end portion being a portion of the radiation probe configured to be in contact with a contact region of the body, and wherein the camera and the monitor enable observation of the contact region.

9. The chair-type phototherapy device according to claim 1, further comprising a treatment light source installed inside the radiation probe and configured to emit the radiation light, wherein the radiation probe front end portion is configured to come into contact with the body to cover a radiation field of the radiation light emitted from the treatment light source.

10. The chair-type phototherapy device according to claim 1, further comprising:

a treatment light source installed inside the radiation probe and configured to emit the radiation light; and a sensor at the radiation probe front end portion for detecting whether the radiation probe front end portion is in contact with the body, wherein, based on the sensor detecting that the radiation probe front end portion is in contact with the body, the treatment light source is permitted to emit the radiation light.

11. The chair-type phototherapy device according to claim 1, wherein the camera is one of a plurality of cameras configured to acquire a plurality of images.

12. The chair-type phototherapy device according to claim 1, further comprising:

a treatment light source installed inside the radiation probe and connected to the casing, wherein the casing further comprises a casing protrusion portion which is positioned outside the radiation probe on a connection surface of the casing with the treatment light source and the radiation probe and surrounds the radiation probe at an outside of the camera, and wherein a front end of the casing protrusion portion is positioned in flush with or behind the radiation probe front end portion.

13. The chair-type phototherapy device according to claim 12, further comprising an illumination light source on an inner side of the casing protrusion portion.

14. The chair-type phototherapy device according to claim 1, wherein the ratchet mechanism comprises a rack and pinion mechanism.

* * * * *